United States Patent
Uy et al.

(10) Patent No.: US 10,993,635 B1
(45) Date of Patent: May 4, 2021

(54) INTEGRATING BIOSENSOR TO COMPRESSION SHIRT TEXTILE AND INTERCONNECT METHOD

(71) Applicant: Flextronics AP, LLC, Broomfield, CO (US)

(72) Inventors: William Uy, San Jose, CA (US); Weifeng Liu, Dublin, CA (US); Dason Cheung, Fremont, CA (US); Jie Lian, San Jose, CA (US); Christian Biederman, Scotts Valley, CA (US); Anwar Mohammed, San Jose, CA (US); Murad Kurwa, San Jose, CA (US)

(73) Assignee: Flextronics AP, LLC, Broomfield, CO (US)

( * ) Notice: Subject to any disclaimer, the term of this patent is extended or adjusted under 35 U.S.C. 154(b) by 1052 days.

(21) Appl. No.: 15/077,278

(22) Filed: Mar. 22, 2016

(51) Int. Cl.
*A61B 5/0416* (2006.01)
*A61B 5/00* (2006.01)

(52) U.S. Cl.
CPC .......... *A61B 5/0416* (2013.01); *A61B 5/6804* (2013.01)

(58) Field of Classification Search
CPC ... A61B 5/0416; A61B 5/6804; A61B 5/0006; A61B 5/02438; A61B 5/02444; A61B 5/6805; A61B 5/0002; A61B 5/486; A61B 5/0245; A61B 5/04085
See application file for complete search history.

(56) References Cited

U.S. PATENT DOCUMENTS

| | | | |
|---|---|---|---|
| 2,649,267 A | 8/1953 | Luke | |
| 3,830,991 A | 8/1974 | Durocher | |
| 4,017,697 A | 4/1977 | Larson | |
| 4,855,537 A | 8/1989 | Nakai et al. | |
| 5,433,735 A | 7/1995 | Zanakia | |
| 5,479,138 A | 12/1995 | Kuroda et al. | |
| 5,626,135 A * | 5/1997 | Sanfilippo | A61B 5/0408 600/391 |
| 5,675,299 A | 11/1997 | Suski | |
| 6,388,556 B1 | 5/2002 | Imai | |
| 6,483,055 B1 | 11/2002 | Tanabe | |
| 6,743,982 B2 | 6/2004 | Biegelsen | |
| 6,830,668 B2 | 12/2004 | Musho | |
| 7,022,917 B2 | 4/2006 | Jung | |

(Continued)

OTHER PUBLICATIONS

Final office action dated Mar. 29, 2019. U.S. Appl. No. 14/724,673, filed May 28, 2015, Applicant: Weifeng Liu, 27 p[ages.

(Continued)

*Primary Examiner* — Eun Hwa Kim
*Assistant Examiner* — Adam Z Minchella
(74) *Attorney, Agent, or Firm* — Haverstock & Owens LLP (57) ABSTRACT

An electronic sensor device has one or more sensor electrodes and one or more electrical conductors printed on a substrate. Textile layers are attached on either side of the substrate with access to the electrical conductors provided by a conductive snap assembly. The substrate can be a TPU (thermoplastic polyurethane) film. The sensor can be a biosensor, and the biosensor is attached to a compression textile, such as a compression shirt, and electrically interconnected using printed conductive ink interconnects to a conductive snap button.

22 Claims, 6 Drawing Sheets

(56) References Cited

U.S. PATENT DOCUMENTS

| | | | |
|---|---|---|---|
| 7,072,721 B1* | 7/2006 | Trent | A61N 1/0484 607/149 |
| 7,112,755 B2 | 9/2006 | Kitano | |
| 7,504,904 B1 | 3/2009 | Powers et al. | |
| 7,528,337 B2 | 5/2009 | Tanabe | |
| 8,207,473 B2 | 6/2012 | Axisa | |
| 8,282,232 B2 | 10/2012 | Hsu | |
| 8,552,730 B2 | 10/2013 | Chiao | |
| 8,560,044 B2* | 10/2013 | Kurzweil | A61B 5/01 600/386 |
| 8,587,385 B2 | 11/2013 | Umeda | |
| 9,148,949 B2 | 9/2015 | Zhou | |
| 9,174,042 B2 | 11/2015 | Schonenberger | |
| 9,651,514 B2 | 5/2017 | Soccol | |
| 9,674,950 B1 | 6/2017 | Liu | |
| 9,706,648 B2 | 7/2017 | Zhou | |
| 9,826,633 B2 | 11/2017 | Cherenack | |
| 9,832,863 B2 | 11/2017 | Elsherbini | |
| 9,839,123 B2 | 12/2017 | Van Keymeulen | |
| 9,883,583 B2 | 1/2018 | Cousins | |
| 2004/0009729 A1 | 1/2004 | Hill | |
| 2004/0094835 A1 | 5/2004 | Maghribi | |
| 2004/0243204 A1 | 12/2004 | Maghribi | |
| 2004/0244193 A1 | 12/2004 | Jung | |
| 2006/0131158 A1 | 6/2006 | Takiguchi | |
| 2006/0135863 A1* | 6/2006 | Birnbaum | A61B 5/0002 600/388 |
| 2006/0258205 A1 | 11/2006 | Locher | |
| 2007/0215883 A1 | 9/2007 | Dixon | |
| 2008/0093118 A1 | 4/2008 | Takahashi | |
| 2008/0099230 A1 | 5/2008 | Takahashi | |
| 2008/0139953 A1* | 6/2008 | Baker | A61B 5/0006 600/509 |
| 2008/0258314 A1 | 10/2008 | Yoo | |
| 2008/0288026 A1 | 11/2008 | Cross | |
| 2009/0229876 A1 | 9/2009 | Takahashi | |
| 2010/0014265 A1 | 1/2010 | Sagisaka | |
| 2010/0018634 A1 | 1/2010 | Takahashi | |
| 2010/0025087 A1 | 2/2010 | Takahashi | |
| 2010/0037947 A1 | 2/2010 | Anelevitz | |
| 2010/0063365 A1* | 3/2010 | Pisani | A61B 5/0002 600/301 |
| 2010/0160762 A1* | 6/2010 | McLaughlin | A61B 5/0416 600/372 |
| 2010/0185076 A1* | 7/2010 | Jeong | A61B 5/0408 600/388 |
| 2011/0067904 A1 | 3/2011 | Aoyama | |
| 2011/0180307 A1 | 7/2011 | Naganuma | |
| 2011/0198111 A1 | 8/2011 | Naganuma | |
| 2011/0199739 A1 | 8/2011 | Naganuma | |
| 2012/0032224 A1 | 2/2012 | Fang | |
| 2012/0052268 A1 | 3/2012 | Axisa | |
| 2012/0165633 A1* | 6/2012 | Khair | A61B 5/04085 600/345 |
| 2012/0238910 A1* | 9/2012 | Nordstrom | A61B 5/02444 600/587 |
| 2012/0325524 A1 | 12/2012 | Naganuma | |
| 2013/0019383 A1* | 1/2013 | Korkala | A61B 5/6804 2/338 |
| 2013/0060115 A1* | 3/2013 | Gehman | A61B 5/0416 600/372 |
| 2013/0176737 A1 | 7/2013 | Zhou | |
| 2014/0015633 A1 | 1/2014 | Nakae | |
| 2014/0209690 A1 | 7/2014 | Teng | |
| 2014/0343390 A1* | 11/2014 | Berzowska | D04B 1/225 600/388 |
| 2015/0065840 A1 | 3/2015 | Bailey | |
| 2015/0114689 A1 | 4/2015 | Ishihara | |
| 2015/0114690 A1 | 4/2015 | Ishihara | |
| 2015/0148646 A1 | 5/2015 | Park | |
| 2015/0201856 A1 | 7/2015 | Stork | |
| 2015/0366504 A1* | 12/2015 | Connor | A61B 5/0492 600/301 |
| 2016/0160403 A1 | 6/2016 | Van Keymeulen | |
| 2016/0270727 A1* | 9/2016 | Berg | A61B 5/0006 |
| 2016/0361015 A1 | 12/2016 | Wang | |
| 2017/0099729 A1 | 4/2017 | Kim et al. | |
| 2017/0170799 A1 | 6/2017 | Kong et al. | |
| 2017/0172421 A1* | 6/2017 | Dabby | A61B 5/0205 |
| 2017/0315657 A1 | 11/2017 | Lai | |
| 2017/0365644 A1 | 12/2017 | Zheng | |
| 2017/0370030 A1 | 12/2017 | Podhajny | |
| 2018/0180574 A1 | 6/2018 | Paul | |
| 2018/0249767 A1* | 9/2018 | Begriche | A61B 5/0492 |
| 2019/0234814 A1 | 8/2019 | Yoon | |

OTHER PUBLICATIONS

Non-Final Office Action, U.S. Appl. No. 16/016,138, filed Jun. 22, 2018, Applicant: Mark Bergman, dated Dec. 23, 2019, 19 pages.

* cited by examiner

INTEGRATING BIOSENSOR TO COMPRESSION SHIRT TEXTILE AND INTERCONNECT METHOD

FIELD OF THE INVENTION

The present invention is generally directed to the field of electronic sensor devices. More specifically, the present invention is directed to an electronic sensor device having through hole via interconnect using ink printing.

BACKGROUND OF THE INVENTION

A sensor is a device configured to sense or detect some characteristic of its environment. The sensor senses events or changes in a quantity of the characteristic and provides a corresponding output. In an electronic sensor, the output is generally an electrical or optical signal, although there are other forms of output.

Some electronic sensors, referred to as biosensors, are designed to be attached to human or animal skin in order to sense a body characteristic such as the electrical activity of the heat or brain. Examples of such electronic sensors include an electrocardiography (ECG or EKG) sensor and an electroencephalography (EEG) sensor. Electronic sensors for attaching to skin include an electrode which performs the actually sensing and a conductive trace for conducting the corresponding signal. The electrode needs to be in contact with the skin, while the conductive trace needs to be insulated from the skin to prevent current leakage and contamination from sweat.

SUMMARY OF THE INVENTION

Embodiments are directed to an electronic sensor device having one or more sensor electrodes and one or more electrical conductors printed on a substrate. Textile layers are attached on either side of the substrate with access to the electrical conductors provided by a conductive snap assembly. In some embodiments, the substrate is a TPU (thermoplastic polyurethane) film. In some embodiments, the sensor is a biosensor, and the biosensor is attached to a compression textile, such as a compression shirt, and electrically interconnected using printed conductive ink interconnects to a conductive snap button.

In an aspect, an electronic sensor device is disclosed. The electronic sensor device comprises a substrate, an electrical conductor, a sensor electrode, encapsulant material, an electrically conductive snap assembly, textile material and a control module. The substrate has a first surface and a second surface, and a through hole extending through the substrate from the first surface to the second surface. An electrically conductive ink is printed on the second surface of the substrate to form the electrical conductor. The electrical conductor has a snap assembly interface conductive pad surrounding the through hole, a sensor interface conductive pad, and an interconnect electrically interconnecting the snap assembly interface conductive pad and sensor interface conductive pad. The sensor electrode is printed on the sensor interface conductive pad. The encapsulant material covers the interconnect, around a perimeter of the sensor electrode, and around a perimeter of the snap assembly interface conductive pad leaving exposed from the encapsulant material a surface of the sensor electrode and a surface of the snap assembly interface conductive pad. The electrically conductive snap assembly is positioned through the through hole and electrically coupled to the snap assembly interface conductive pad. The textile material covers the first surface of the substrate, the second surface of the substrate and the encapsulant, leaving exposed from the textile material at least a portion of the snap assembly at the second surface of the substrate and the sensor. The control module mechanically and electrically couples to the exposed portion of the snap assembly to form an electrical interconnect between the sensor electrode and the control module. In some embodiments, the substrate comprises one of a thermoplastic polyurethane film or urethane. In some embodiments, the electrically conductive ink comprises one of a silver ink, a copper ink or a carbon ink. In some embodiments, the sensor electrode comprises one of an ECG sensor or an EKG sensor. In some embodiments, the sensor electrode comprises one of a Ag based gel or a AgCl based gel. In some embodiments, the textile material comprises a compression textile shirt. In some embodiments, the snap assembly comprises a snap button socket and the control module comprises a snap button ball configured to attach to the snap button socket.

In another aspect, a method of fabricating an electronic sensor device is disclosed. The method includes providing a substrate having a first surface and a second surface. The method also includes printing an electrically conductive ink on the second surface of the substrate to form an electrical conductor having a sensor interface conductive pad, a snap assembly interface conductive pad, and an interconnect electrically interconnecting the snap assembly interface conductive pad and sensor interface conductive pad. The method also includes printing a sensor electrode on the sensor interface conductive pad. The method also includes applying an encapsulant material on the interconnect, around a perimeter of the sensor electrode, and around a perimeter of the snap assembly interface conductive pad leaving exposed from the encapsulant material a surface of the sensor electrode and a surface of the snap assembly interface conductive pad. The method also includes forming a through hole extending through the substrate and the snap assembly interface conductive pad. The method also includes positioning an electrically conductive snap assembly through the through hole and electrically coupling the snap assembly to the snap assembly interface conductive pad. The method also includes covering the first surface of the substrate, the second surface of the substrate and the encapsulant with a textile material, leaving exposed from the textile material at least a portion of the snap assembly at the second surface of the substrate and the sensor. The method also includes mechanically and electrically coupling a control module to the exposed portion of the snap assembly to form an electrical interconnect between the sensor electrode and the control module. In some embodiments, the electrically conductive ink is printed in the shape of a conductive trace. In some embodiments, the substrate comprises one of a thermoplastic polyurethane film or urethane. In some embodiments, the electrically conductive ink comprises one of a silver ink, a copper ink or a carbon ink. In some embodiments, the sensor electrode comprises one of an ECG sensor or an EKG sensor. In some embodiments, the sensor electrode comprises one of a Ag based gel or a AgCl based gel. In some embodiments, the textile material comprises a compression textile shirt. In some embodiments, the snap assembly comprises a snap button socket and the control module comprises a snap button ball configured to attach to the snap button socket. In some embodiments, the method further includes curing the electrically conductive ink to form the electrical conductor. In some embodiments, the method further includes curing the sensor electrode. In some embodiments, the textile material comprises a first textile layer and a second textile layer, further wherein covering the first surface of the substrate, the second surface of the substrate and the encapsulant with the textile material comprises covering the first surface of the substrate with the first textile layer and covering the second surface of the substrate and the encapsulant with the second textile layer. In some embodiments, the method further includes stitching the first textile layer to the second textile layer. In some embodiments, the method further includes laminating the first textile layer, the substrate, the encapsulant material and the second textile layer.

BRIEF DESCRIPTION OF THE DRAWINGS

Several example embodiments are described with reference to the drawings, wherein like components are provided with like reference numerals. The example embodiments are intended to illustrate, but not to limit, the invention. The drawings include the following figures.

DETAILED DESCRIPTION OF THE EMBODIMENTS

Embodiments of the present application are directed to an electronic sensor device. Those of ordinary skill in the art will realize that the following detailed description of the electronic sensor device is illustrative only and is not intended to be in any way limiting. Other embodiments of the electronic sensor device will readily suggest themselves to such skilled persons having the benefit of this disclosure.

Reference will now be made in detail to implementations of the electronic sensor device as illustrated in the accompanying drawings. The same reference indicators will be used throughout the drawings and the following detailed description to refer to the same or like parts. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
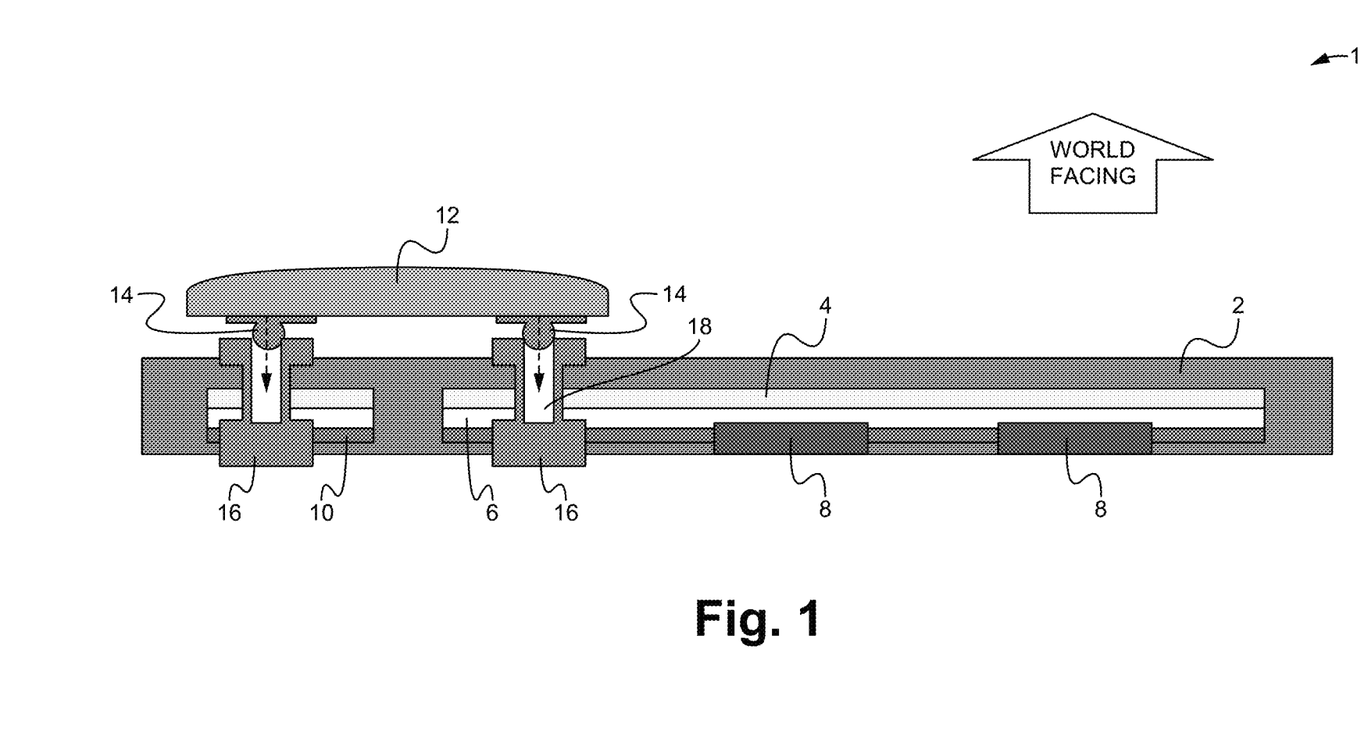
FIG. 1 illustrates a cut-out side view of an electronic sensor device according to an embodiment.

FIG. 1 illustrates a cut-out side view of an electronic sensor device according to an embodiment. The electronic sensor device 1 includes textile material 2, a substrate 4, stretchable conductive interconnects 6, stretchable conductive sensors electrodes 8, encapsulant material 10, a control module 12, conductive snap buttons 14, and snap assemblies 16. In some embodiments, the substrate 4 is a film. An example of a substrate material includes, but is not limited to, a TPU (thermoplastic polyurethane) film. In general, the substrate 4 is made of an electrically non-conductive material. In some embodiments, the substrate 4 is made of a flexible, stretchable material.

The substrate 4 includes a through hole 18, which extends through an entire thickness of the substrate 4. Conductive interconnects 6 are formed on a first surface of the substrate 4. The conductive interconnects 6 can be shaped and positioned to form electrical conductors that can be part of or electrically connected to an external electrical conductor such as a wire, to an external electrical interface for external connection or to an external electrical device such as the control module 12. The conductive interconnects 6 are made of an electrically conductive ink. Examples of inks that can be used for the electrically conductive ink include, but are not limited to, a silver ink, a copper ink or a carbon ink.

The sensor electrodes, or sensors, 8 are formed on the conductive interconnects 6. The sensors 8 can take on a variety of shapes, sizes and positions on the second surface 6 according to the intended application. For example, the sensors 8 can be configured as an EKG or ECG sensor electrode or an EEG sensor electrode. It is understood that the sensors 8 can be configured as other types of sensors. The sensors 8 are made of an electrically conductive material. In some embodiments, the sensors 8 are made of a silver (Ag) based gel or a AgCl based gel. Alternatively, the sensors 8 can be made of printed silver ink, silver chloride, conductive rubber material or conductive cloth. The encapsulant material 10 is formed on the conductive interconnects 6, leaving exposed the sensors 8 and the snap assemblies 16.

Each snap assembly 16 includes a first component and a second component that are connected through the through hole 8. The snap assemblies 16 are made of electrically conductive material and are electrically connected to the conductive interconnects 6. Textile material 2 is attached to either side of the substrate 4 and corresponding conductive interconnects 6 and encapsulant material 10. The textile material 2 forms exterior surfaces of the electronic sensor device 1 except where the sensors 8 and the snap assemblies 16 are left uncovered. Examples of textile materials include, but are not limited to, spandex, denim, leather other equivalent material to which the substrate 4, such as TPU film, can be laminated. A preferred textile material is spandex to maximize contact/connectivity of the stretchable conductive sensors electrodes 8 with underlying skin. In some embodiments, the textile material 2 is made of a compression textile, such as a compression shirt. High compression fabrics such as spandex, nylon, polyester material and other equivalent can be used. In general, material used for the textile material 2 can include, but are not limited to, cotton, wool, nylon, polyester or other synthetic or natural materials commonly used in clothing.

Conductive snap buttons 14 are mechanically attached and provide electrical interconnections to the control module 12. The conductive snap buttons 14 are configured to mechanically attach and provide electrical interconnections to the snap assemblies 16.

Figure 2:
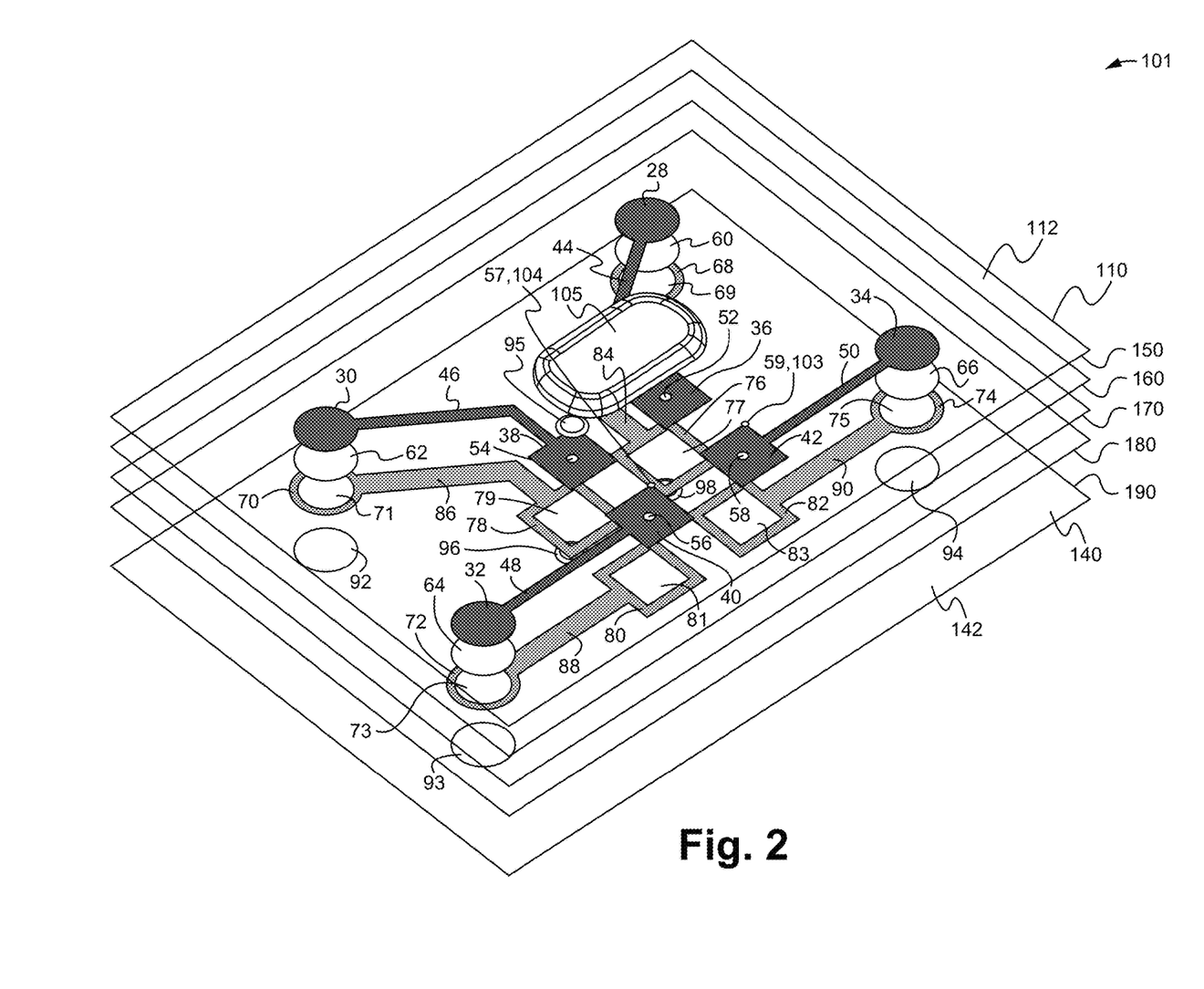
FIG. 2 illustrates a top down exploded view of another electronic device according to an embodiment.

FIG. 2 illustrates a top down exploded view of another electronic device according to an embodiment. The components of the electronic sensor device 101 are exploded into various planes shown in FIG. 2. A plane 150 shows a textile layer 110. The textile layer 110 includes a first surface 112 and an opposing second surface (not shown). A plane 160 shows conductive interconnected patterns including sensor interface conductive pads, snap assembly interface conductive pads and interconnections between the two. A plane 170 shows sensors. A plane 180 shows encapsulant material. A plane 190 shows a textile layer 140. The textile layer 140 includes a first surface 142 and an opposing second surface 144 (FIG. 7). The electronic sensor device 101 also includes a substrate 100 (FIGS. 3-6) which is not shown in FIG. 2 but is positioned between the planes 150 and 160.

FIGS. 3-10 illustrate various method steps of fabricating an electronic sensor device according to an embodiment. The method shown in FIGS. 3-10 is shown and described in terms of the electronic sensor device 101 of FIG. 2. It is understood that the method steps can be generally applied to make alternatively configured electronic sensor devices. FIGS. 3-5 and 7 show bottom-up views relative to the top-down perspective view of FIG. 2 and therefore results in the reversed reference numeral numbering when comparing FIG. 2 side by side with FIGS. 3-5 and 7. At the step 200 shown in FIG. 3, a substrate 100 is provided. In this exemplary configuration, a TPU film is selected and provided as the substrate 100. The substrate 100 includes a first surface 102 (FIG. 6) and an opposing second surface 104. Conductive ink is applied to second surface 104 of the TPU substrate 100 to form conductive pads and interconnects. In some embodiments, the conductive ink is printed onto the substrate 100. In some embodiments, the conductive ink is stretchable. The conductive ink can be silver ink, copper ink or carbon ink. The conductive ink is applied as a pattern that includes multiple conductive pads for interfacing with subsequent sensors. In the exemplary configuration shown in FIGS. 3-10, there are four such sensor interface conductive pads 28, 30, 32, 34 formed by the conductive ink as sensor interfaces. The conductive ink pattern also includes multiple conductive pads for interfacing with subsequent snap assemblies. In the exemplary configuration shown in FIGS. 3-10, there are four such conductive pads 36, 38, 40, 42 formed by the conductive ink as snap assembly interfaces. In some embodiments, each snap assembly interface conductive pad 36, 38, 40, 42 is formed having a hole 52, 54, 56, 58, respectively, approximately in the center of each conductive pad. Each hole is an absence of conductive ink and is sized such that a snap assembly component fits within the hole providing an electrical interconnection between the snap assembly interface conductive pad and the snap assembly. The conductive ink pattern also includes multiple interconnects for electrical interconnection between one of the sensor interface conductive pads and one of the snap assembly interface conductive pads. In the exemplary configuration shown in FIGS. 3-10, a conductive interconnect 44 interconnects the sensor interface conductive pad 28 to the snap assembly interface conductive pad 36, a conductive interconnect 46 interconnects the sensor interface conductive pad 30 to the snap assembly interface conductive pad 38, a conductive interconnect 48 interconnects the sensor interface conductive pad 32 to the snap assembly interface conductive pad 40, and a conductive interconnect 50 interconnects the sensor interface conductive pad 34 to the snap assembly interface conductive pad 42. Although the configuration shown in FIG. 3 includes four conductive interconnected patterns, it is understood that more or less than four such patterns can be formed using conductive ink.

Figure 3:
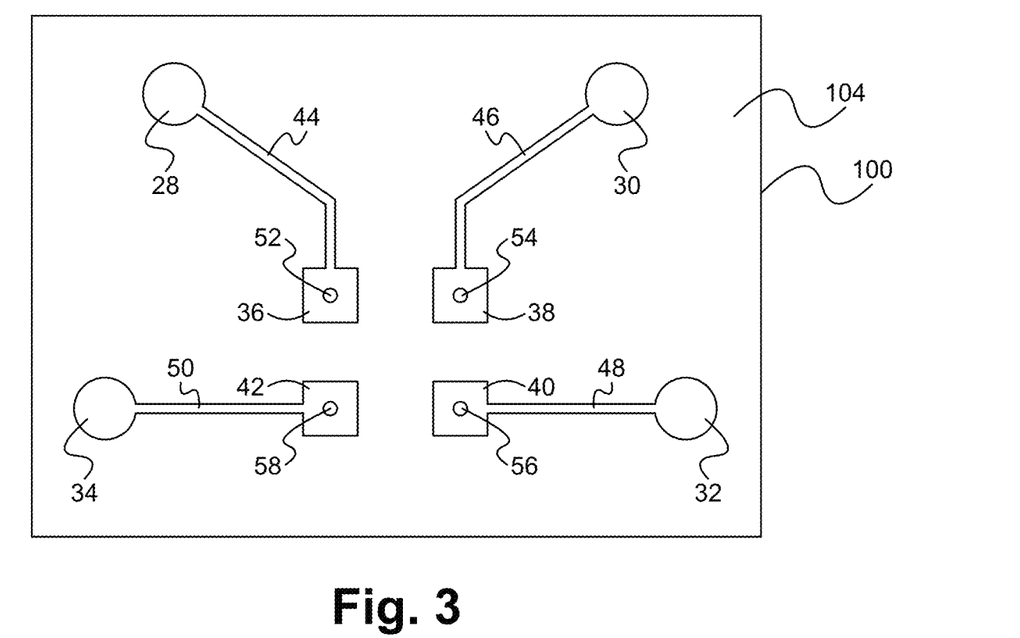
FIGS. 3-10 illustrate various method steps of fabricating an electronic sensor device according to an embodiment.

In some embodiments, an ink jet printer is used to dispense the electrically conductive ink used to form the conductive ink pattern. Alternatively, other types of printers can be used to dispense the electrically conductive ink onto the second surface 104. After application of the electrically conductive ink onto the second surface 104, the electrically conductive ink is cured. The cured electrically conductive ink forms the conductive pads and interconnects.

Figure 4:
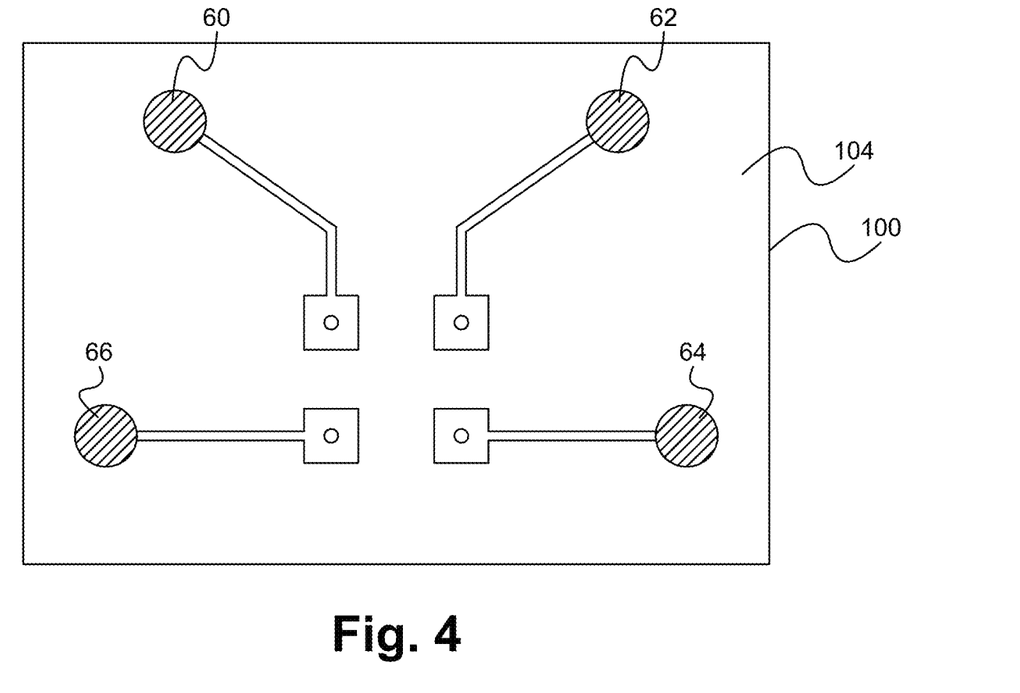

At the step 210 shown in FIG. 4, sensor ink is applied onto the sensor interface conductive pads 28, 30, 32, 34 to form sensors 60, 62, 64, 66, respectively. In some embodiments, a footprint of each sensor 60, 62, 64, 66 matches a footprint of the corresponding underlying sensor interface conductive pad 28, 30, 32, 34. In other embodiments, the footprint of each sensor 60, 62, 64, 66 is slightly smaller than the footprint of the corresponding underlying sensor interface conductive pad 28, 30, 32, 34. In some embodiments, an ink jet printer is used to dispense the sensor ink used to form the sensors 60, 62, 64, 66. Alternatively, other types of printers can be used to dispense the sensor ink onto the sensor interface conductive pad 28, 30, 32, 34. After application of the sensor ink onto the sensor interface conductive pad 28, 30, 32, 34, the sensor ink is cured. The cured sensor ink forms the sensors 60, 62, 64, 66.

Figure 5:
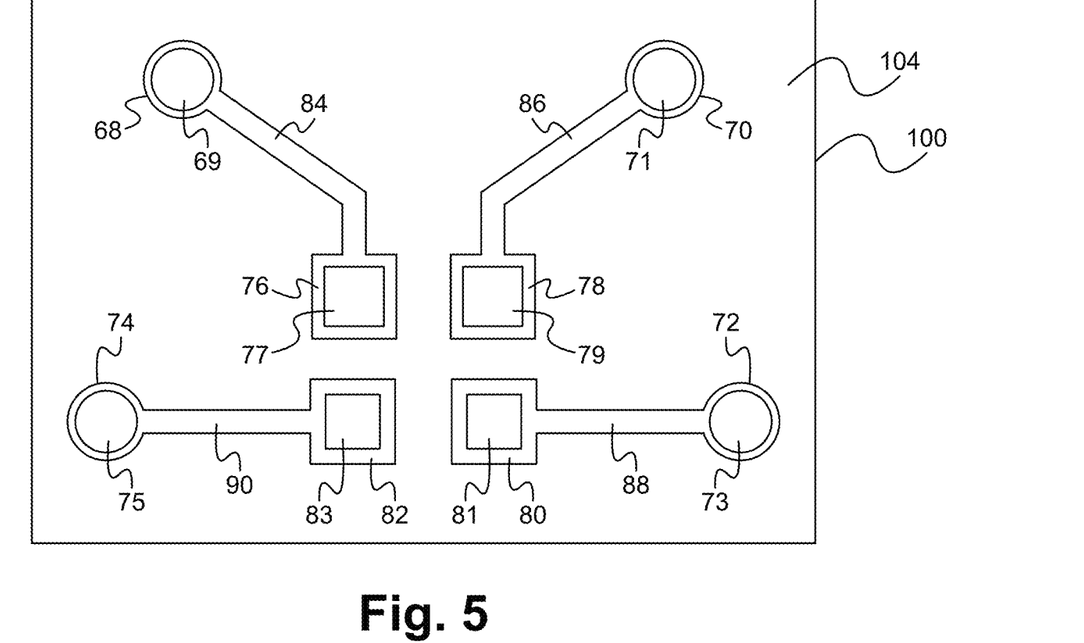

At the step 220 shown in FIG. 5, an encapsulation material is applied. The encapsulation material is applied such that encapsulant portions 84, 86, 88, 90 cover the conductive interconnects 44, 46, 48, 50 (FIG. 3), respectively. The encapsulant material is also applied such that encapsulant portions 68, 70, 72, 74 surround the sensors 60, 62, 64, 66, respectively. Holes 69, 71, 73, 75 in the encapsulant material leave exposed a surface of each sensor 60, 62, 64, 66. In embodiments where the footprint of each sensor 60, 62, 64, 66 is slightly smaller than the footprint of the corresponding underlying sensor interface conductive pads 28, 30, 32, 34, the encapsulant portions 68, 70, 72, 74 cover the exposed portions of the sensor interface conductive pads 28, 30, 32, 34. The encapsulant material is also applied such that encapsulant portions 76, 78, 80, 82 surround the snap assembly interface conductive pads 36, 38, 40, 42, respectively. Holes 77, 79, 81, 83 in the encapsulant material leave exposed a surface of each snap assembly interface conductive pad 36, 38, 40, 42. In some embodiments, encapsulant portions 76, 78, 80, 82 overlap a perimeter portion of the snap assembly interface conductive pads 36, 38, 40, 42 while still leaving exposed a surface of each snap assembly interface conductive pads 36, 38, 40, 42.

Figure 6:
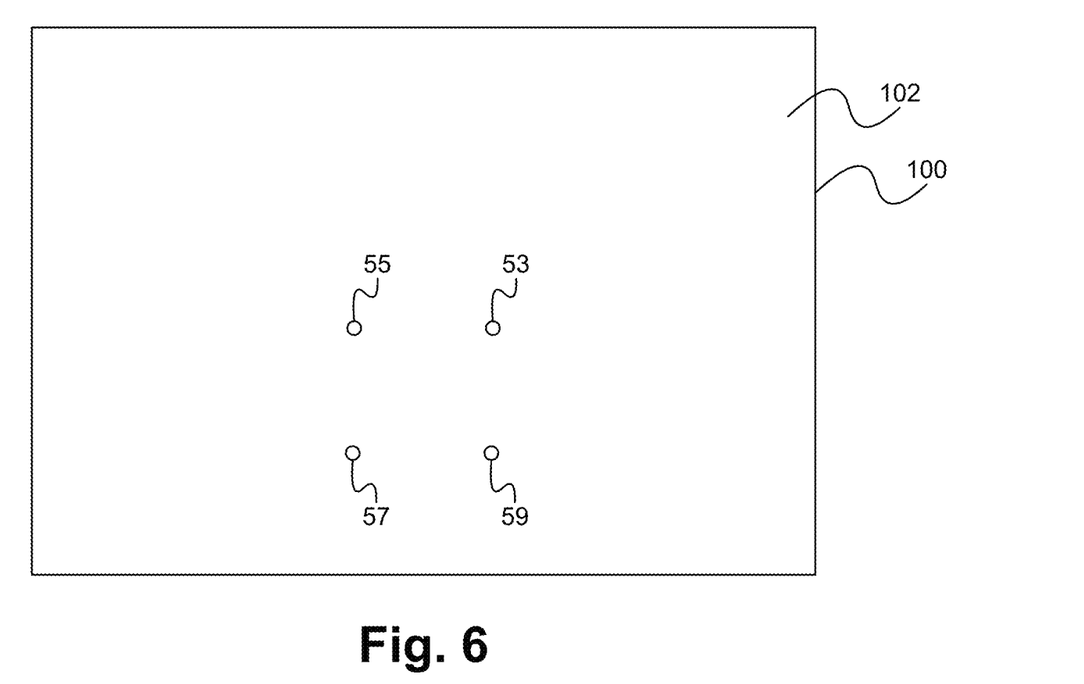
Figure 7:
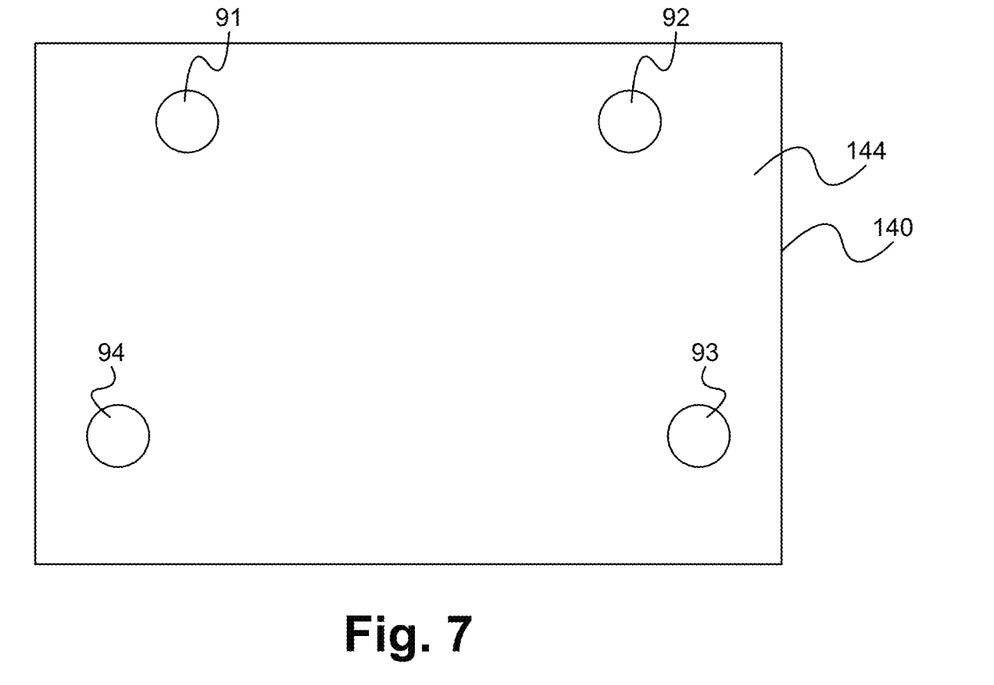

At the step 230 shown in FIG. 6, holes 53, 55, 57, 59 are made through the substrate 100. FIG. 6 shows a top-down view of the first surface 102 of the substrate 100. Each hole 53, 55, 57, 59 in the substrate 100 is aligned with a corresponding one of the holes 52, 54, 56, 58, respectively, in the snap assembly interface conductive pads 36, 38, 40, 42. In some embodiments, the holes 53, 55, 57, 59 are formed using a punch hole device. It is understood that alternative techniques can be used to form the holes 53, 55, 57, 59. In general, depending on the type of material selected for the substrate 100, any known technique or device can be used for forming a through hole in the selected material.

At the step 240 shown in FIG. 7, a textile layer 140 is attached to the substrate 100 such that a first surface 142 (FIG. 2) of the textile layer 140 faces the second surface 104 of the substrate 100. Holes 91, 92, 93, 94 in the textile layer 140 can be pre-formed or formed after attachment of the textile layer 140 to the substrate 100. The holes 91, 92, 93, 94 are positioned so as to align with the sensors 60, 62, 64, 66, respectively, thereby exposing the sensors 60, 62, 64, 66 through the textile layer 140. In some embodiments, the textile layer 140 and the substrate 100 are laminated together.

Figure 8:
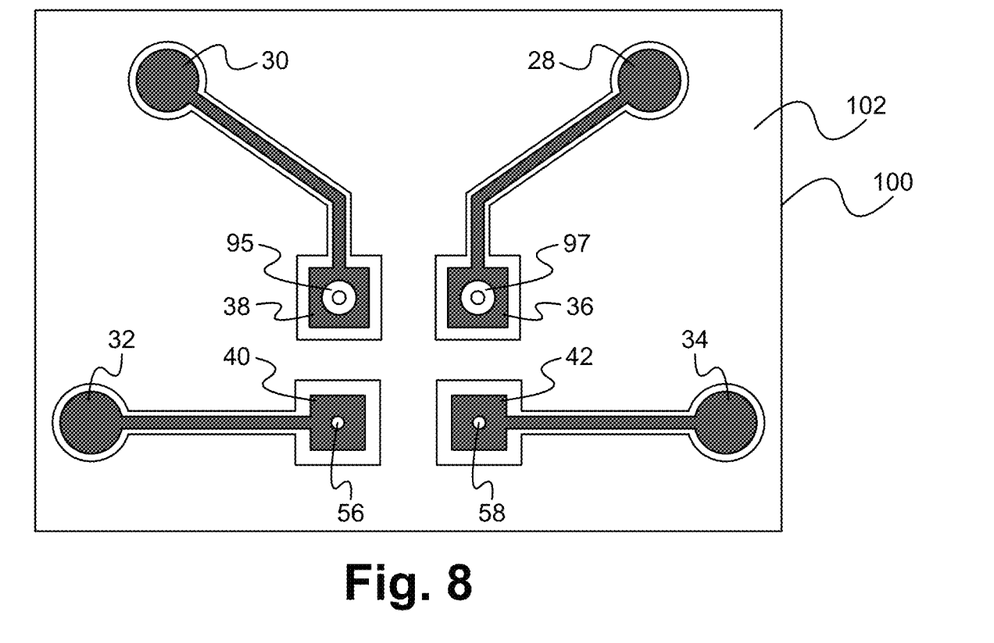

FIG. 8 shows a top down view of the first surface 102 of the substrate 100 where the substrate material is transparent to better show the positions of the conductive interconnects and pads applied to the opposite second surface 104 of the substrate 100. At the step 250 shown in FIG. 8, snap assemblies are attached to the laminated substrate/textile layer formed in step 240. In some embodiments, each snap assembly includes two components, such as a snap button and a snap button rivet. In a first snap assembly, a first component 95, such as a snap button top, is paired with a second component 96 (FIG. 2), such as a snap button rivet. The first component 95 includes a snap button having a ball socket into which an external snap button ball can be attached and a stem extending from an opposing side of the snap button socket. The stem extends at least partially into the hole 55 in the substrate 100 and in some embodiments through the hole 54 in the snap assembly interface conductive pad 38 and couples with the second component 96. In some embodiments, the second component 96 includes a rivet that extends at least partially into the hole 54 and in some embodiments into the hole 55. The first component 95 contacts the snap assembly interface conductive pad 38 thereby forming an electrical interconnection between the two. In some embodiments, the first component 95 and the second component 96 couple together with the textile layer 140 in between. In other embodiments, a hole is formed in the textile layer 140 so that the first component 95 is coupled directly to the second component 96. Similarly, a second snap assembly having first component 97 and second component 98 (FIG. 2) is attached. FIG. 8 shows two snap assemblies. It is understood that additional snap assemblies can be attached at the two remaining snap assembly conductive pads 40 and 42.

Figure 9:
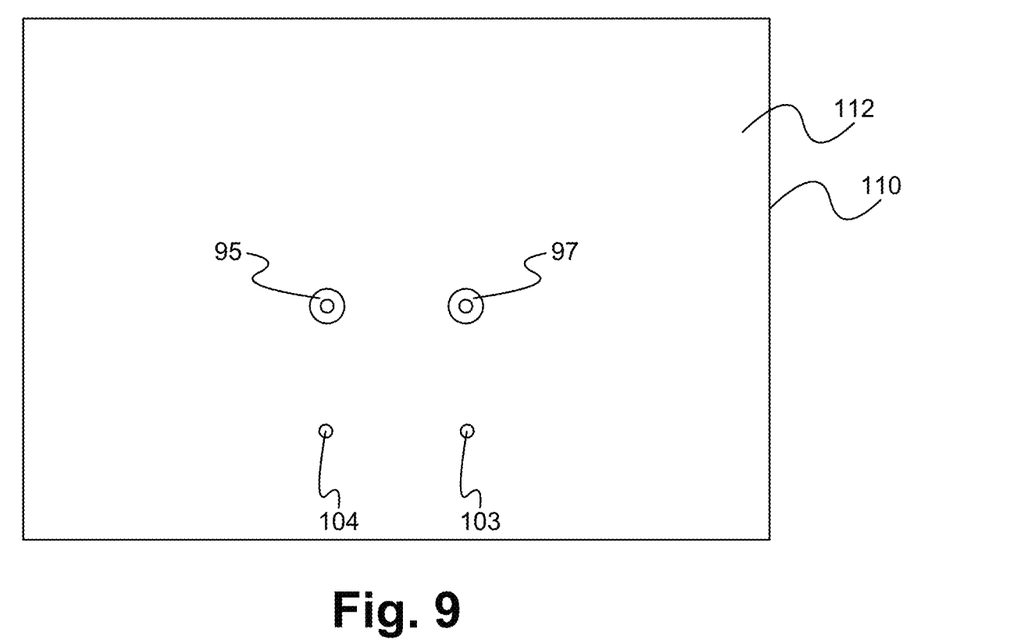

At the step 260 shown in FIG. 9, a textile layer 110 is attached to the substrate 100 such that a second surface (not shown) of the textile layer 110 faces the first surface 102 (FIG. 8) of the substrate 100. Holes 101 (not shown, underneath first component 95), 102 (not shown, underneath first component 97), 103, 104 in the textile layer 110 are pre-formed prior to attachment of the textile layer 110 to the substrate 100. The holes 101, 102, 103, 104 are positioned so as to align with the first component 95, the first component 97, the hole 59 (FIG. 6) in the substrate 100, the hole 57 (FIG. 6) in the substrate 100, respectively. As the textile layer is flexible and stretchable, the first components of the snap assemblies can be pushed through the holes in the textile layer. In some embodiments, the textile layer 110, the substrate 100 and the textile layer 140 are laminated together. In other embodiments, the textile layer 110 is sewn to the textile layer 140 at corresponding positions of overlap.

Figure 10:
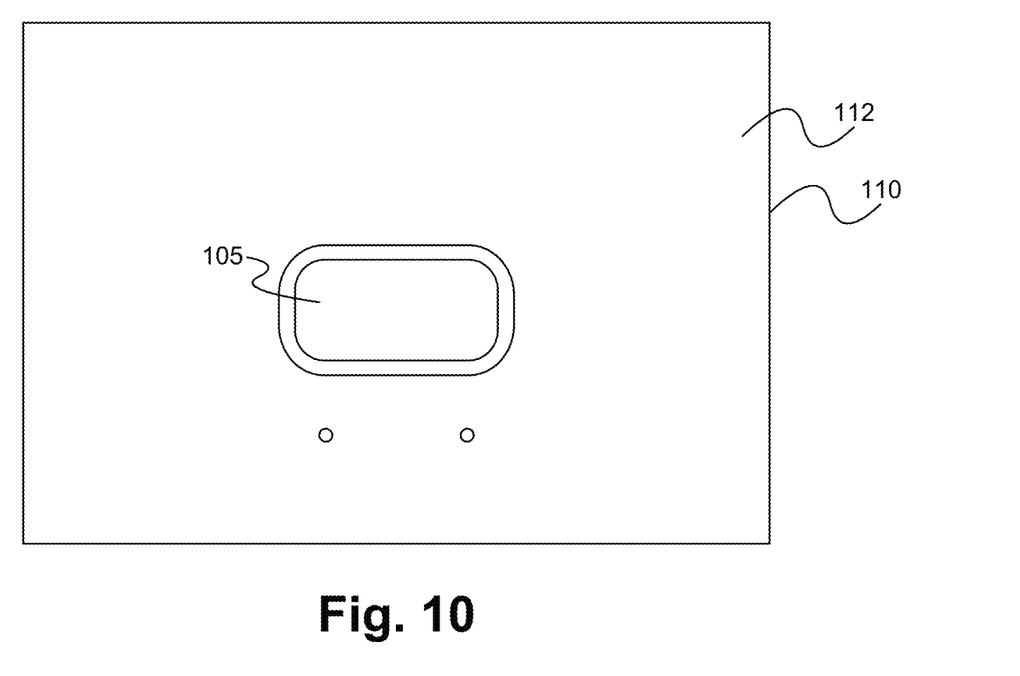

At the step 270 shown in FIG. 10, a control module 105 is attached to the snap assemblies. The control module 105 includes conductive snap buttons (underside of control module 105) that snap into first components 95, 97 (FIG. 9) of two snap assemblies to mechanically connect and form electrically conductive interconnections between the control module 105 and the snap assemblies. The control module 105 can include a wireless transceiver for communicating with an external electronic device. Although FIGS. 2 and 10 show the control module connected at two snap assemblies, it is understood that the electronic sensor device can be configured with a control module, electrical conductors and snap assemblies for more than two interconnecting points with the control module.

It is understood that the order of the various steps described above can be interchanged, rearranged or combined. For example, the snap assemblies can be attached to the substrate 100 prior to attaching the textile layer 140 such that the first component and the second component of each snap button assembly directly contact each other without an intervening textile layer. The resulting configuration has the second component of each snap assembly covered by the textile layer 140 and not exposed at an external surface of the electronic sensor device. As another example, both textile layers 110 and 140 can be concurrently attached to the substrate 100 during the same step. As yet another example, the snap assembly interface conductive pads 36, 38, 40, 42 can be initially formed without holes, and when the holes 53, 55, 57, 59 in the substrate 100 are formed, the holes 52, 54, 56, 58 in the snap assembly interface conductive pads 36, 38, 40, 42 can be concurrently formed. Other examples are also contemplated.

The present application has been described in terms of specific embodiments incorporating details to facilitate the understanding of the principles of construction and operation of the electronic sensor device. Many of the components shown and described in the various figures can be interchanged to achieve the results necessary, and this description should be read to encompass such interchange as well. As such, references herein to specific embodiments and details thereof are not intended to limit the scope of the claims appended hereto. It will be apparent to those skilled in the art that modifications can be made to the embodiments chosen for illustration without departing from the spirit and scope of the application.

What is claimed is:

1. An electronic sensor device comprising:
  a. a non-conductive substrate having a first surface and a second surface, and a through hole extending through the non-conductive substrate from the first surface to the second surface;
  b. an electrically conductive ink printed on the second surface of the non-conductive substrate, wherein the electrically conductive ink forms an electrical conductor that is a separate and distinct layer from the non-conductive substrate, further wherein the electrical conductor includes having a snap assembly interface conductive pad surrounding the through hole, a sensor interface conductive pad, and an interconnect electrically interconnecting the snap assembly interface conductive pad and sensor interface conductive pad, further wherein the through hole extends through the snap assembly interface conductive pad;
  c. a sensor electrode printed on the sensor interface conductive pad;
  d. an encapsulant material covering the interconnect, around a perimeter of the sensor electrode, and around a perimeter of the snap assembly interface conductive pad leaving exposed from the encapsulant material a surface of the sensor electrode and a surface of the snap assembly interface conductive pad;
  e. an electrically conductive snap assembly positioned through the through hole and electrically coupled to the snap assembly interface conductive pad, wherein the electrically conductive snap assembly comprises a first component and a second component that are connected to each other;
  f. a textile material covering the first surface of the non-conductive substrate, the second surface of the non-conductive substrate and the encapsulant, leaving exposed from the textile material at least a portion of the snap assembly at the first surface of the non-conductive substrate and the sensor electrode; and
  g. a control module mechanically and electrically coupled to the exposed portion of the electrically conductive snap assembly to form an electrical interconnect between the sensor electrode and the control module.

2. The electronic sensor device of claim 1 wherein the non-conductive substrate comprises one of a thermoplastic polyurethane film or urethane.

3. The electronic sensor device of claim 1 wherein the electrically conductive ink comprises one of a silver ink, a copper ink or a carbon ink.

4. The electronic sensor device of claim 1 wherein the sensor electrode comprises one of an electrocardiogram (ECG) sensor or an electroencephalogram (EEG) sensor.

5. The electronic sensor device of claim 1 wherein the sensor electrode comprises one of a silver (Ag) based gel or a silver chloride (Ag/Cl) based gel.

6. The electronic sensor device of claim 1 wherein the textile material comprises a compression textile shirt.

7. The electronic sensor device of claim 1 wherein the electrically conductive snap assembly comprises a snap button socket and the control module comprises a snap button ball configured to attach to the snap button socket.

8. The electronic sensor device of claim 1 wherein the first component of the electrically conductive snap assembly is a snap button and the second component is a snap button rivet, further wherein the electronic sensor device further comprises a conductive snap button ball coupled to the control module, and the snap button ball is detachably coupled to the snap button of the electrically conductive snap assembly.

9. A method of fabricating an electronic sensor device, the method comprising:
   a. providing a non-conductive substrate having a first surface and a second surface;
   b. printing an electrically conductive ink on the second surface of the non-conductive substrate to form an electrical conductor that is a separate and distinct layer from the non-conductive substrate, further wherein the electrical conductor includes having a sensor interface conductive pad, a snap assembly interface conductive pad, and an interconnect electrically interconnecting the snap assembly interface conductive pad and sensor interface conductive pad,
   c. printing a sensor electrode on the sensor interface conductive pad;
   d. applying an encapsulant material on the interconnect, around a perimeter of the sensor electrode, and around a perimeter of the snap assembly interface conductive pad leaving exposed from the encapsulant material a surface of the sensor electrode and a surface of the snap assembly interface conductive pad;
   e. forming a through hole extending through the substrate and the snap assembly interface conductive pad;
   f. positioning an electrically conductive snap assembly through the through hole and electrically coupling the electrically conductive snap assembly to the snap assembly interface conductive pad, wherein the electrically conductive snap assembly comprises a first component and a second component that are connected to each other;
   g. covering the first surface of the non-conductive substrate, the second surface of the non-conductive substrate and the encapsulant with a textile material, leaving exposed from the textile material at least a portion of the electrically conductive snap assembly at the first surface of the non-conductive substrate and the sensor electrode; and
   h. mechanically and electrically coupling a control module to the exposed portion of the electrically conductive snap assembly to form an electrical interconnect between the sensor electrode and the control module.

10. The method of claim 9 wherein the electrically conductive ink is printed in a shape of a conductive trace.

11. The method of claim 9 wherein the non-conductive substrate comprises one of a thermoplastic polyurethane film or urethane.

12. The method of claim 9 wherein the electrically conductive ink comprises one of a silver ink, a copper ink or a carbon ink.

13. The method of claim 9 wherein the sensor electrode comprises one of an electrocardiogram (ECG) sensor or an electroencephalogram (EEG) sensor.

14. The method of claim 9 wherein the sensor electrode comprises a silver (Ag) based gel or a silver chloride (Ag/Cl) based gel.

15. The method of claim 9 wherein the textile material comprises a compression textile shirt.

16. The method of claim 9 wherein the electrically conductive snap assembly comprises a snap button socket and the control module comprises a snap button ball configured to attach to the snap button socket.

17. The method of claim 9 further comprising curing the electrically conductive ink to form the electrical conductor.

18. The method of claim 9 further comprising curing the sensor electrode.

19. The method of claim 9 wherein the textile material comprises a first textile layer and a second textile layer, further wherein covering the first surface of the non-conductive substrate, the second surface of the non-conductive substrate and the encapsulant with the textile material comprises covering the first surface of the non-conductive substrate with the first textile layer and covering the second surface of the non-conductive substrate and the encapsulant with the second textile layer.

20. The method of claim 19 further comprising stitching the first textile layer to the second textile layer.

21. The method of claim 19 further comprising laminating the first textile layer, the non-conductive substrate, the encapsulant material and the second textile layer.

22. The method of claim 9 wherein the first component of the electrically conductive snap assembly is a snap button and the second component is a snap button rivet, further wherein the electronic sensor device further comprises a conductive snap button ball coupled to the control module, and the snap button ball is detachably coupled to the snap button of the electrically conductive snap assembly.

* * * * *